United States Patent [19]

Ouelette

[11] Patent Number: 4,842,580
[45] Date of Patent: Jun. 27, 1989

[54] COLONIC IRRIGATOR

[76] Inventor: Gloria Ouelette, 2829A Dundas Street West, Apartment 2, Toronto, Ontario, Canada

[21] Appl. No.: 137,586

[22] Filed: Dec. 24, 1987

[30] Foreign Application Priority Data

Jan. 6, 1987 [CA] Canada ..................... 526774

[51] Int. Cl.$^4$ ............................................. A61M 1/00
[52] U.S. Cl. ..................... 604/30; 128/750; 604/43; 604/246; 604/275
[58] Field of Search ........... 604/27, 28, 30, 31, 604/32, 33, 34, 35, 39, 41, 43, 164, 165, 166, 167, 170, 275, 276, 277, 278, 279, 40, 42, 44, 45, 269, 246, 902; 128/200.18, 750

[56] References Cited

U.S. PATENT DOCUMENTS

| Re. 21,615 | 11/1940 | Irwin | 604/35 |
|---|---|---|---|
| 665,371 | 1/1901 | Dumphrey | 604/275 |
| 1,596,847 | 8/1926 | Mallory | 604/40 |
| 1,710,701 | 4/1929 | Hertzberg | 604/41 |
| 1,902,418 | 3/1933 | Pilgrim | 604/43 |
| 2,157,614 | 5/1939 | Lazarus | 604/32 |
| 2,257,072 | 9/1941 | Coombs | 604/35 |
| 2,458,719 | 1/1949 | McCormick | 604/33 |
| 2,873,739 | 2/1959 | Whann | 604/35 |
| 3,042,039 | 7/1962 | Dahlstrom | 604/30 |
| 3,955,573 | 5/1976 | Hansen et al. | 604/269 |
| 4,637,814 | 1/1987 | Leiboff | 604/27 |

FOREIGN PATENT DOCUMENTS

| 133153 | 7/1901 | Fed. Rep. of Germany | 604/39 |
|---|---|---|---|
| 659363 | 4/1934 | Fed. Rep. of Germany | 604/39 |

*Primary Examiner*—C. Fred Rosenbaum
*Assistant Examiner*—Mario Costantino
*Attorney, Agent, or Firm*—William T. Howell

[57] ABSTRACT

A gravity supplied irrigator for colon cleansing has an open ended nozzle with the inner end tapered to accommodate a removable rounded nose obturator extending from the inner end with the body of the round nose obturator bearing against the inner surface of the inner end. A gravity actuated fluid supply to the irrigator is provided by a conduit leading into the nozzle intermediate of its ends and the obturator is removable through the nozzle in order for the fluid supply to enter the irrigator. The conduit supply is preferably offset in relation to the longitudinal axis of the nozzle to provide a swirling action to the entering fluid. The nozzle has an outwardly extending circumferential flange intermediate of the inner end and the conduit, which flange limits the insertion of the irrigator. A conduit attached to the other end of the nozzle has variable control means thereon to control the pressure of fluid in the nozzle and its rate of discharge from said nozzle.

5 Claims, 3 Drawing Sheets

4,842,580

COLONIC IRRIGATOR

FIELD OF THE INVENTION

This invention relates to an irrigator which has the purpose of cleansing the colon of a human being after the irrigator has been inserted into the rectum.

PRIOR ART

Many irrigating devices for the colon have been developed and used, the common feature being that the wash fluid flows into the colon by the force of gravity through the irrigator positioned in the rectum and after sufficient pressure has been created, the flow inwards is stopped and the effect of pressure increase causes the fluid, with the waste content, to flow out of the irrigator; the process is repeated until the desired result of cleansing is achieved.

Some of the known irrigators are quite complicated as a number of factors have to be considered in design in order for it to function properly and with the requisite efficiency. One factor is to ensure progressive cleansing of the colon bearing in mind the limitation of pressure which it can stand without discomfort. Another factor is to ensure that the outgoing fluid, with its suspended waste products, does not contaminate the supply of the incoming fluid and it is desirable to minimise the need to sterilise the irrigator after it has been used or prior to the subsequent use. Another important factor is to ensure that there is no damage to the tissues on insertion into the rectum.

SUMMARY OF THE INVENTION

It is an object of the invention to provide a simple, functional irrigator to progressively cleanse the colon after insertion into the rectum. The irrigator of the invention comprises an open-ended nozzle with the opening at the one, or inward end, in relation to its insertion into the rectum, tapered to bearingly engage the body of a removable rounded nose obturator in order to close the tapered inner end, with the nose of the obturator protruding therefrom after insertion of the nozzle into the rectum. Intermediate of the inward and outward ends of the nozzle is an outwardly extending flange which bears against the anus after the irrigator has been inserted into the rectum. The purpose of the flange is to limit the entry of the irrigator into the rectum but in cases of extreme disability, it also serves the purpose of preventing fluid from escaping around the irrigator and not through it, as desired.

It is one feature of the invention that the nozzle has a gravity actuated fluid supply conduit connected thereto at a position removed from the tapered inner opening with respect to the circumferential flange. Furthermore, this conduit is preferably offset in relation to the longitudinal axis of the cylindrical member so that the fluid entering the latter adopts a spiral movement which materially assists the cleansing action of the irrigator. The offset may only be of a few degrees and as little as 3°, for instance, is sufficient to provide the spiral movement of the fluid for cleansing. The fluid supply conduit previous to its entry into the nozzle is angled away from the circumferential flange.

It is a further feature of the invention that the removable obturator is attached to a spindle which traverses the nozzle longitudinally, one end of the spindle being attached to the obturator and the other end terminating in a stop which bears against the outward end of the cylindrical member; the stop serves to ensure that the obturator is in bearing relation to the inward tapered end of the nozzle when it is inserted into the rectum, thus ensuring a painless entry of the obturator. To permit ingress of the fluid from the conduit supply, the obturator is withdrawn from the nozzle through the outward end of the irrigator after insertion in the rectum and the outward end of the irrigator is connected to a take away tube for egress of the contaminated fluid. The take away tube has variable control means thereon to control the pressure of fluid in the nozzle and its rate of discharge from said nozzle.

It is a further feature of the invention that the cylindrical member is reduced in diameter adjacent the flange on the side of the inward opening, the purpose of this reduction is to accommodate the sphincter muscle at the entrance to the rectum.

DESCRIPTION OF THE DRAWINGS

The invention will now be described in relation to the accompanying drawings in which.

DESCRIPTION OF A PREFERRED EMBODIMENT

Figure 1:
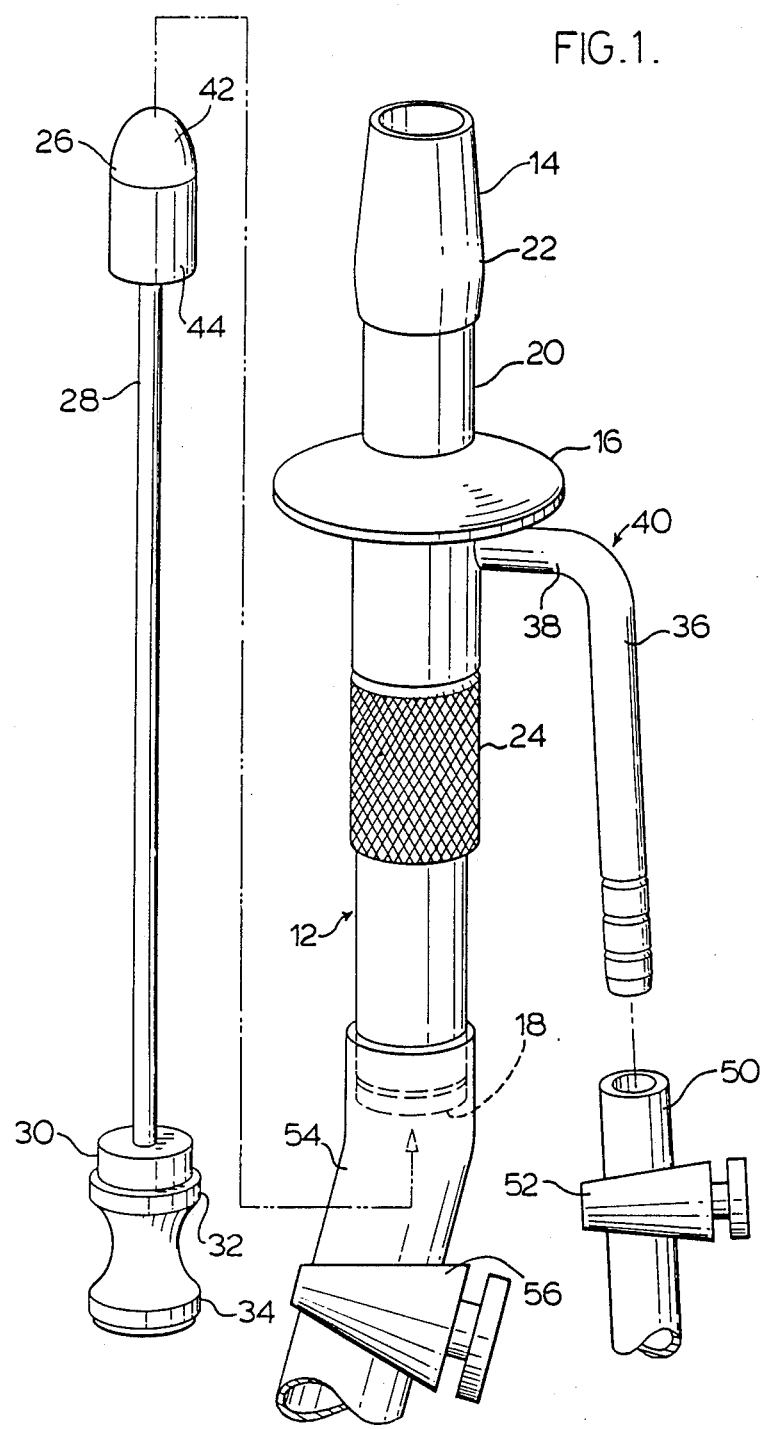
FIG. 1 is an exploded view of a colonic irrigator constructed according to a preferred embodiment of the invention.

With reference to the drawings, there is shown in FIG. 1 an open ended nozzle generally denoted by the numeral 12 and it has a tapered, inner end portion 14 with a circumferential dish shaped flange 16 intermediate of the tapered end and the other or outward open end 18. Adjacent the flange 16 and inward thereof, is a portion 20 of the reduced diameter in relation to the widest part 22 of the tapered end portion 14.

Figure 2:
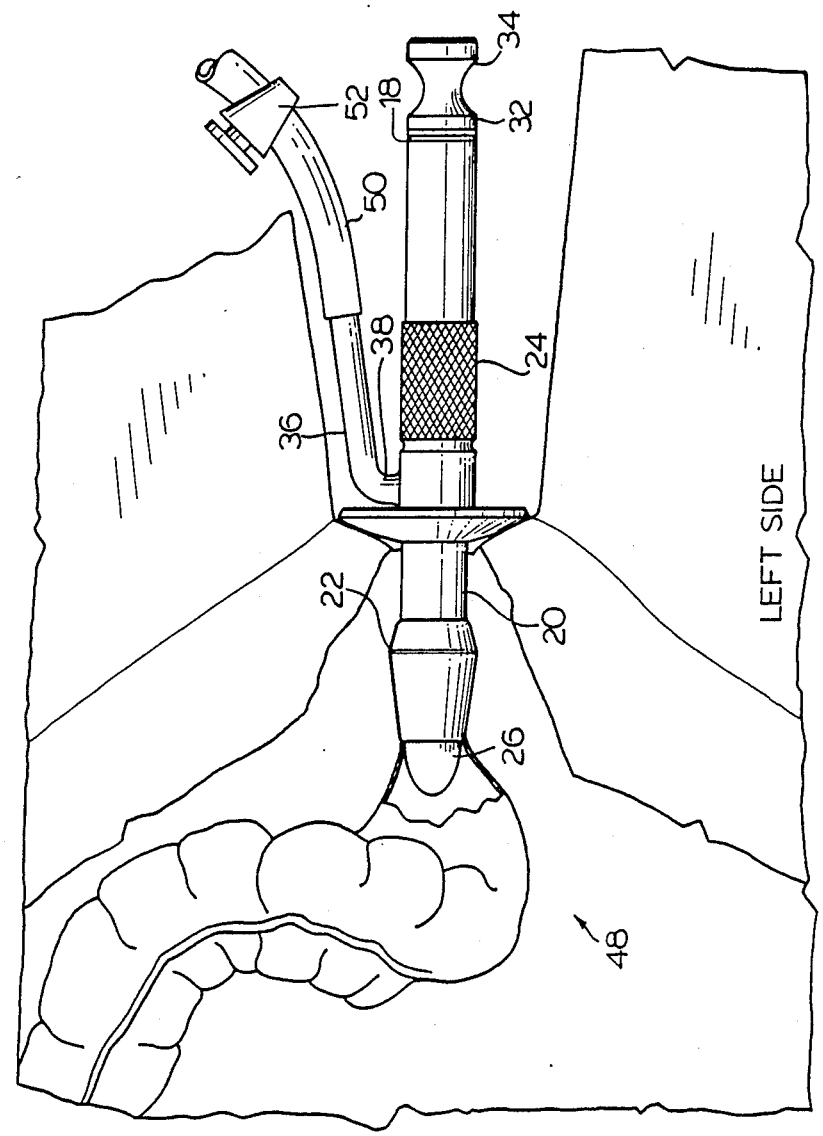
FIG. 2 is a view of an irrigator constructed according to FIG. 1 but positioned in the rectum before the oburator has been withdrawn.

The nozzle is also shown in FIGS. 1 and 2 to have a serrated portion 24 between the flange 16 and the outward end 18. The purpose of this serrated portion 24 is to provide a grip on the otherwise smooth surface of the irrigator during its insertion into the rectum as shown in FIG. 2. The nozzle 12 carries a rounded nose oburator 26 which projects from the tapered inward open end 14 as shown in FIG. 2 after insertion into the rectum, the body of the obturator 26 bearing against the inner surface of the tapered open end 14. As shown in FIG. 1, the obturator 26 may be withdrawn from the nozzle 12 and for this purpose the obturator 26 is attached to a spindle 28 which traverses the nozzle 12. The spindle 28 terminates in an integral collar 30 and when the obturator 26 is in place as shown in FIG. 3, the collar is located inside the outward open end 18 of the nozzle 12.

Figure 3:
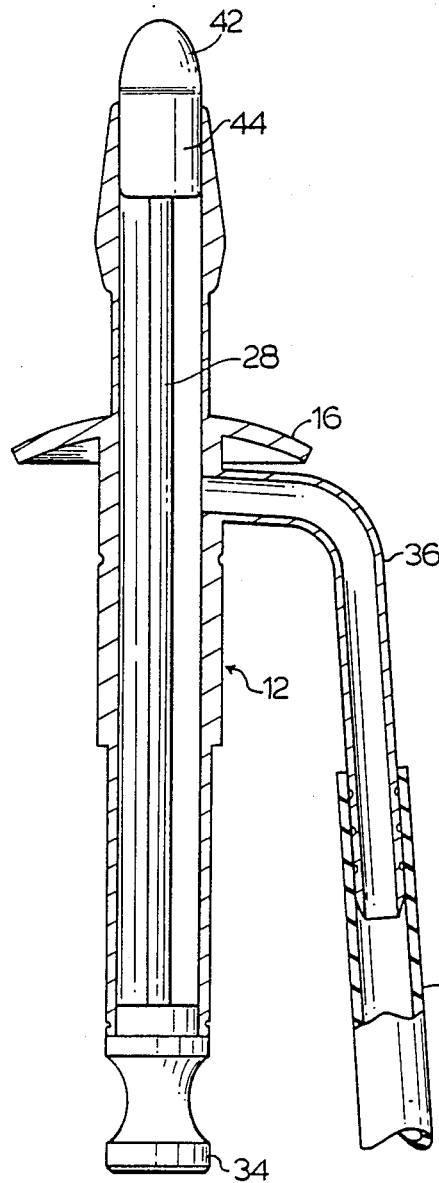
FIG. 3 is a cross section of an assembled irrigator constructed according to the preferred embodiment shown in FIG. 1.
Figure 4:
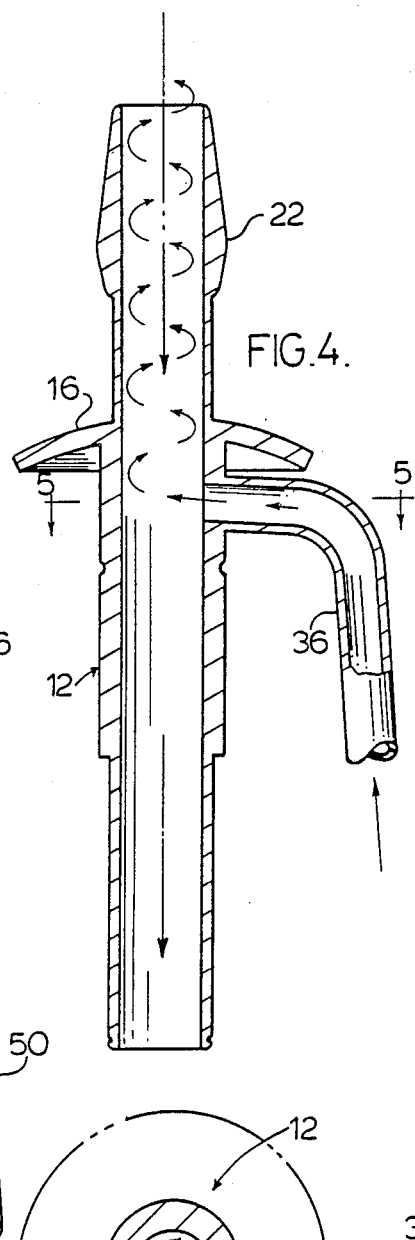
FIG. 4 is a cross section of the embodiment shown in FIG. 3 with the obturator withdrawn and showning the flows inward and outward of the fluid and FIG. 5 is a cross section taken on the lines 5—5 of FIG. 4 illustrating the offset of the conduit supply in relation to the irrigator and the resulting spiral flow of the incoming fluid.

The collar 30 has an integral flange 32 which bears against the outward end 18 of the nozzle 12 as shown in FIG. 3. The flange 32 terminates in a handle 34, conventionally shaped as shown.

Figure 5:
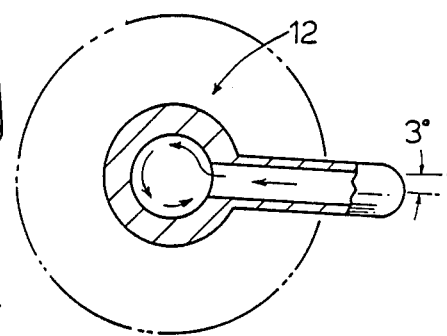

The construction of the irrigator is completed by a conduit 36 which enters the nozzle 12 adjacent to the dish shaped flange 16, see FIG. 1, on the side opposite to the inner open end 14. It is a preferred feature of the invention that the conduit is slightly offset in relation to the longitudinal axis of the nozzle 12 as shown in FIGS. 2 and 5 with the result that the fluid entering the nozzle 12 is directed to one side and adopts a spiral, or swirling, path which enhances the cleansing action. The conduit 36 is removably connected to a gravity actuated fluid supply not shown and may be controlled, if necessary, by a valve 52.

The conduit 36 has a substantially vertical portion 38 at its entry into the nozzle 12 and the portion 38 is bent normally at 40 so that the conduit 36 leads away to the rear of the irrigator. The obturator 26 has a rounded nose 42 on a base 44 and on insertion of the irrigator as shown in FIG. 2, the base 44 of the rounded nose head 42 is in bearing relation to the tapered inward end portion 14 with the nose 42 protruding from the nozzle 12. This relation provides a smooth transition between the two parts and results in painless entry of the irrigator into the rectum.

The bearing relation referred to above is ensured by locating the flange 32 on the spindle 28 at a position so that on abutment of the flange 32 with the outer end 18 of the nozzle 12, the obturator body 44 will always bear against the inner end surface 14 of the nozzle 12.

The operation of the irrigator is simple and briefly described. As shown in FIG. 2, it is inserted into the rectum and this to a predetermined extent about 40 mm, which distance is ensured by contact of the dish shaped flange 16 with the body. Prior to insertion of the irrigator, the patient lies on the left side to straighten the sigmoid which is the lower part of the colon, and generally denoted by the numeral 48, while ensuring that the conduit tube 36 is located above the cylindrical member 12. The obturator 26 is then withdrawn and the conduit tube 36 is connected to the fluid source through a flexible tube 50 which may be provided with a closure valve 52 simply to stop the flow before and after operating the irrigator. Next, the open outward end 18 is connected to a conduit 54 provided with a control valve 56, which conduit 54 leads to waste. The control valve 56 is variably operable to control the pressure of the fluid in the nozzle and its rate of discharge therefrom. The supply of fluid commences with the opening of the valve 52 and this continues until the pressure is built up to the extend that it should be relieved at which time the valve 56 is opened for variable control of the flow of waste fluid.

It will be appreciated that the waste fluid can never enter the conduit 36 whether the valve 50 is open or closed as the pressure is always against the emerging fluid. This is of great value as it minimizes the possibility of contamination of the incoming cleansing fluid.

The location of the supply tank to provide sufficient pressure is a matter for experiment as is also the drop necessary for the waste to flow away on adjusting the opening of the control valve 56. The diameter of the widest part 22 of the tapered portion 14 of the nozzle 12 is about 15 mm for use on patients who have no rectal problems whilst the preferred offset of the conduit 36 is about 3° and this is sufficient to provide the spiralling action of the incoming cleansing fluid which may only be warm water.

The provision of the normally disposed bend at 40 on the conduit 36 which directs the latter rearwardly not only provides for better handling but also reduces the chance of contamination of the incoming supply by the outgoing fluid.

I claim:

1. A colonic irrigator for insertion through the rectum of a prostrate person comprising an open ended nozzle, a flange on said nozzle intermediate of its ends, a tapered one end to said nozzle, a conduit for delivering gravity fed irrigating fluid downward to said nozzle and attached thereto between said flange and the other end of said nozzle, a rounded nose obturator head adapted for bearing location in said tapered end, said obturator head projecting therefrom, a spindle traversing said nozzle, secured at one end to said obturator head and at the other end to a stop bearing against the other end of said nozzle, said stop limiting the travel of said obturator head in said nozzle for said bearing relationship, said spindle being adapted to permit manual removal of said obturator head after insertion into the rectum, another conduit attachable to said other end of said nozzle after said obturator has been withdrawn and valve means on said another conduit adapted to variably control the discharge of fluid from said nozzle thereby varying the pressure of fluid acting on the colon.

2. A colonic irrigator according to claim 1 wherein said nozzle has a reduced outside diameter portion intermediate of said flange and said tapered end.

3. A colonic irrigator for insertion through the rectum of a prostrate person comprising an open ended nozzle, a flange on said nozzle intermediate of its ends, a tapered one end to said nozzle, a conduit for delivering gravity fed irrigating fluid downward to said nozzle and attached thereto between said flange and the other end of said nozzle, said conduit where it is attached to the nozzle, being offset in relation to the longitudinal axis of said nozzle to define means for inducing spiral action to the entering fluid, a rounded nose obturator head adpated for bearing location in said tapered end, said obturator head projecting therefrom, a spindle traversing said nozzle, secured at one end to said obturator head and at the other end to a stop bearing against the other end of said nozzle, said stop limiting the travel of said obturator head in said nozzle for said bearing relationship, said spindle being adapted to permit manual removal of said obturator head after insertion into the rectum, another conduit attachable to said other end of said nozzle after said obturator has been withdrawn and valve means on said another conduit adapted to variably control the discharge of fluid from said nozzle thereby varying the pressure of fluid acting on the colon.

4. A colonic irrigator according to claim 2 wherein said nozzle has a reduced outside diameter portion intermediate of said flange and said tapered end.

5. A colonic irrigator according to claim 3 wherein said offset is about 3°.

* * * * *